United States Patent [19]

Ratigan

[11] 4,002,066
[45] Jan. 11, 1977

[54] OCEANOGRAPHIC WATER SAMPLER

[76] Inventor: Edward Ratigan, 170 Birch Hill Road, Locust Valley, N.Y. 11560

[22] Filed: Mar. 4, 1976

[21] Appl. No.: 663,914

[52] U.S. Cl. .......................... 73/170 A; 23/253 R
[51] Int. Cl.² ........................................ G01N 1/12
[58] Field of Search ...... 73/170 A, 425.4 A, 425.2; 23/253 R

[56] References Cited
UNITED STATES PATENTS

| | | | |
|---|---|---|---|
| 3,379,065 | 4/1968 | Gibbon | 73/425.4 R |
| 3,692,490 | 9/1972 | Hall | 73/425.4 R X |
| 3,714,830 | 2/1973 | Keir | 73/425.4 R |
| 3,892,130 | 7/1975 | Winget et al. | 73/425.4 R |

Primary Examiner—Jerry W. Myracle
Attorney, Agent, or Firm—James P. Malone

[57] ABSTRACT

An oceanographic water sampling device. A container has a pair of covers closably mounted and means connected to close the covers. Means are provided to add chemicals to the trapped water in the container at the same location where and when the sample is taken. Ampules containing the chemical are mounted in the container and knives are connected to break the ampules at predetermined times. A time delay device is provided so that a first chemical may be added to the trapped water at a certain time, and the second chemical may be added to the trapped water after a predetermined time delay.

6 Claims, 5 Drawing Figures

OCEANOGRAPHIC WATER SAMPLER

This invention relates to oceanographic water sampling devices and more particularly to such devices wherein chemicals may be added to the trapped water at the time and place where the sample is taken.

The use of conventional water sampling devices, for instance, to measure the quantity of oxygen in the water has several disadvantages.

1. The sample bottle or container must be withdrawn from the ocean and placed in a second bottle, this transfer may permit the entry of additional oxygen.
2. When the reagents used in the test are introduced there is also the possibility of additional oxygen entering.
3. When the sample is brought up from a depth, an adiabatic change takes place and an exchange of heat may affect the oxygen contents of the sample.
4. There is a relatively long time delay before the test can be made with the result that the sample could change temperature which would affect the oxygen content. Time delay may be, for instance, one hour if a large number of samples was taken.

The present invention solves this difficulty by adding the reagents in situ, at the time and place where the sample is taken before any change in the oxygen contents can be made by change of temperature or handling of the sample.

My sampling device has attached a conventional Van Dorn Releasing Device which is not part of my invention, by clamps. The clamps attach around the support plate of the sampling device. The device is attached to a cable 1/16 inch diameter by way of a thumb-screw wire clamp and a wire slot.

The entire apparatus is then lowered by the cable to the desired depth. Activation of the device is accomplished by attaching a metal weight or messenger, to the cable and sliding it down the cable by gravity. The metal weight then hits a plunger cap and forces the plunger down. This action releases a main release arm and allows it to rotate freely.

Attached to the main release arm are three loops of wires all under tension. When the messenger hits the plunger, all three loops are released simultaneously. The action does the following:

The release of the two cover controlling wire loops allows a resilient shock cord to draw the top and bottom covers closed. This results in trapping the sample of water in the bottle.

The release of the third cord starts a piston type clock running. The clock is essentially a piston and cylinder arrangement. The cylinder is filled with water or oil and a needle valve is pre-set for a specific rate of discharge time required. The piston is placed under tension by heavy rubber bands. When the piston cord is released, the piston moves down forcing the fluid out of the cylinder.

As the piston moves down it trips two lever arms at different time intervals. This is accomplished by the two control lines with different amounts of slack in them. As the piston travels down the slack is eventually taken out and a first lever arm is released due to the pull of the line on a swivle trigger. The interval between the release of the lever arms is five to twenty minutes depending on the time setting at the needle valve.

When the first lever arm is released its knives crush two ampules, one containing 2 ml of Mn $SO_4$ and the other, 2 ml of KOH - KI. At the same time that they are crushed, a propellor, propelled by rubber bands, spins and mixes these reagents into solution with the water sample.

When the second lever arm is released, its knife crushes an ampule containing 2 Ml of $H_2SO_4$. This is also mixed into solution by another propellor. All ampules were loaded into the device at the surface and the holes were covered with screw caps with rubber O-rings to prevent the ampules from becoming dislodged and also to prevent the water sample from leaking out.

The entire device is now hauled to the surface where the water sample is then analyzed by the classical winkler titration method for determining dissolved oxygen content.

Accordingly a principal object of the invention is to provide new and improved oceanographic water sampling means.

Another object of the invention is to provide new and improved oceanographic water sampling means having means to add chemicals to the trapped water at the same location where and when the sample is taken.

Another object of the invention is to provide new and improved oceanographic water sampling means having means to add chemicals to the trapped water at the same location where and when the sample is taken wherein ampules are mounted in the container and means are provided for breaking the ampules into the trapped sample for the purpose of making a chemical test on the sample.

Another object of the invention is to provide new and improved oceanographic water sampling means comprising a container cover means closably mounted on the container, means connected to close the cover means to trap a water sample, and means to add chemicals to the trapped water in the container at the same location where the sample is taken.

These and other objects of the invention will be apparent from the following Specification and drawings of which:

Figure 1:
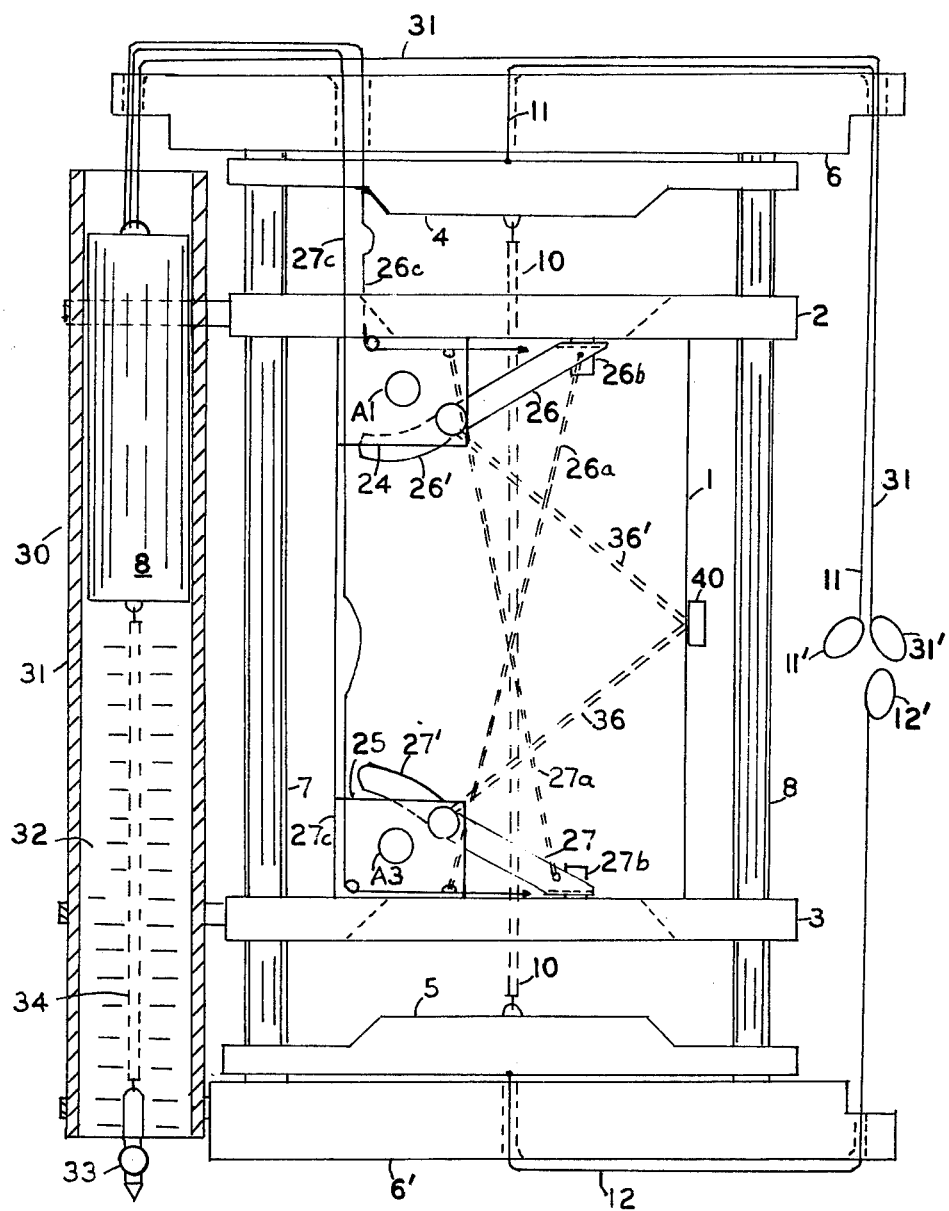
FIG. 1 is a side view of an embodiment of the invention.

Referring to FIG. 1, the invention comprises a hollow container 1, which has two flange rings 2 and 3, top and bottom support plates 6 and 6', a top cover 4, and a bottom cover 5. The covers 4 and 5, are slidably mounted on rods 7, 8, etc., which are mounted in the support plates 6 and 6'. The covers are connected together with a strong elastic member 10, which may be of coiled surgical tubing.

In order to receive the water sample, the covers are initially held apart by means of the control lines 11 and 12, which terminate in loops 11' and 12'.

Figure 2:
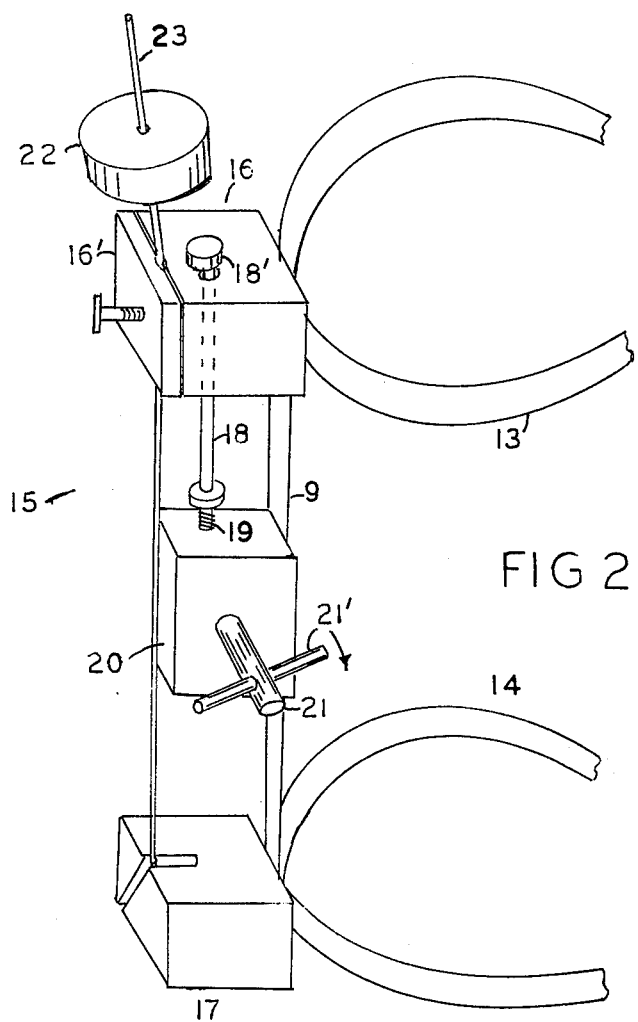
FIG. 2 is a detail view showing a conventional oceanographic sample container releasing device.

Referring to FIG. 2, attached to the flange ring clamps 13 and 14, is a conventional Van Dorn oceanographic sampling relase device 15. The release device comprises upper and lower blocks 16 and 17 connected by member 9, block 16 has a wire clamp 16' for the purpose of clamping the wire which lowers the sampling device into the water. The upper block 16 contains a plunger 18, having a cap 18'. The plunger is spring loaded upwardly by means of the spring 19. The lower end of the plunger 18, terminates in a control block 20, having a conventional latch mechanism so that when the plunger is pushed down the control arm 21, is released. The control arm 21, has a cross arm 21', upon which are mounted the loops of the control cables or wires, 11', 12' and 31'.

When it is desired to actuate the releasing mechanism a metal weight messenger 22 is sent down the wire 23. When the weight 22 hits plunger 18, the plunger will move downwardly and release the control arm 21, which will rotate clockwise because of the pulleys of the cables 11, 12 and 31, FIG. 2, in direction of the arrows, and release the control loops 11', 12' and 31'. When this happens the cover closing resilient member 10 will pull the upper and lower covers 4 and 5 together sealing the container and trapping the water sample. The covers have suitable sealing gaskets.

Figure 3:
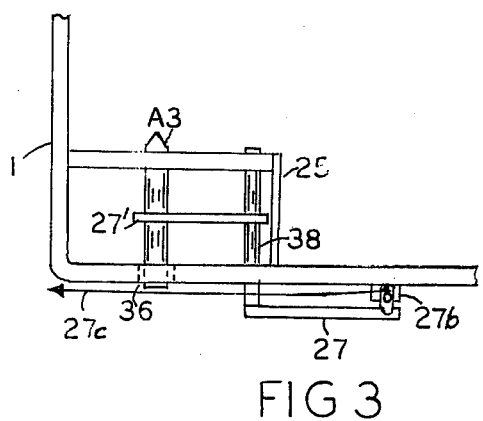
FIG. 3 is a detail view of a lever arm trigger mechanism and ampule holding means of the embodiment of FIG. 1.
Figure 4A:
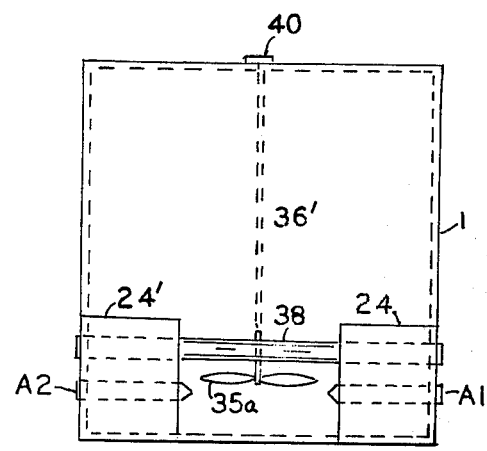
FIG. 4A is a top detail view of a propellor mixing device.
Figure 4:
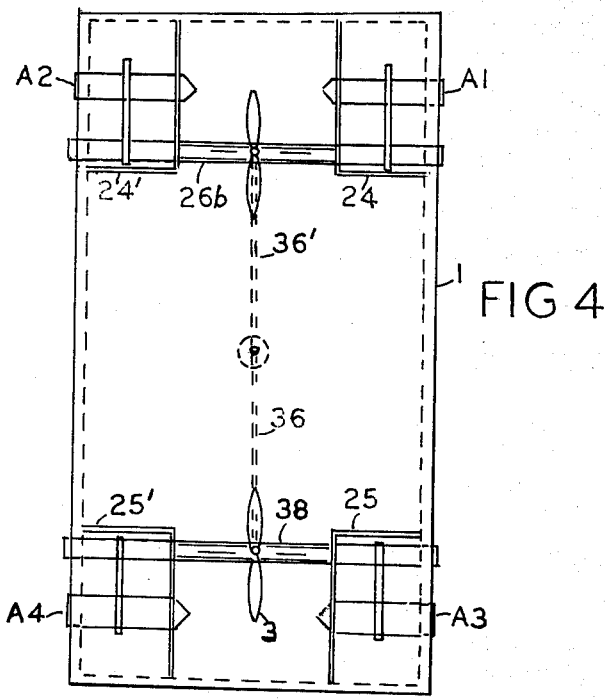
FIG. 4 is a front detail view of a propellor mixing device.

The ampules A1, A2, A3 and A4 are mounted in the side of the container in holding members 24, 24', 25 and 25', as in FIGS. 3 and 4. Lever arms 26 and 27 are pivotally mounted on the holding members 24 and 25 respectively. Mounted on the lever arms are knives 26', 27', which are mounted so that when the lever arms are released the knives will break the ampules. The lever arm 26 is connected to the elastic member 26a and is held in position by means of the trigger 26b, as shown in the detail view of FIG. 3.

Ampule A3 is held in holder 25. The lever arm 27 is similarly connected to the resilient member 27a and is held in position by means of the trigger 27b. The triggers are controlled by the cables 26c and 27c, the other ends of which are connected to the piston 28 of the timing mechanism 30. The timing mechanism is mounted to the support plates 6 and 6' and comprises a cylinder 31, containing a piston 28. The purpose of the timing device is to provide a controlled time interval between the breaking of ampules A1, A2, A3 and A4. The timing mechanism is actuated as follows.

The piston 28 is connected by the cable 31 which has a loop 31' which is mounted on the control arm 21'. The bottom of the cylinder 31 beneath the piston contains a liquid 32 and the bottom of the cylinder is connected to a needle valve 33. The piston is spring loaded in the downward direction by means of the elastic member 34. When the control arm 21 is activated it releases the loop 31' and the piston is drawn downwardly by means of the elastic member 34 at a controlled rate determined by the adjustment of the exhaust needle valve 33. The piston is connected to the triggers of the lever arms by means of the cables 26c, 27c, which have predetermined amounts of slack so that as the piston 28 descends it will first take the slack out of the control cable 26c, and actuate the trigger 26b, FIG. 3, which will release the lever arm 26, which will be rapidly rotated clockwise by means of the elastic member 26a. The knives 26', 26" will also rotate and break the ampules A1 and A2.

At a later time the slack will be taken out of the cable 27c, which will actuate trigger 27b, as shown in FIG. 3, releasing the lever arm 27, which will be rapidly closed by the elastic member 27a, causing the knives 27', 27", to rotate counter clockwise and break the ampules A3 and A4. The time delay between the breaking of the two sets of ampules may be, for instance, between 5 to 20 minutes.

FIG. 4 is a front detail view and FIG. 4A a top detail veiw showing the propellor mechanism. Propellor 35a is mounted on shaft 38 which is the same shaft mounting the knife 27'. The propellor is powered by the rubber band 36 which is wound up by means of the cap 40. When the shaft 38 is in the latched position, the propellor will be restrained by locking of the rubber band. When the shaft is rotated counter clockwise in FIG. 1 as the same time as the ampule is broken then the propellor is also rotated into the plane of the rubber band 36 and is free to rotate. The propellor 35 is similarly mounted on the shaft 26d and is operated in the same manner by the rubber band 36'.

The ampules may be conventional glass ampules containing the desired chemicals. They are inserted into the holding members 24, 25, etc. which are part of the container 1. They are sealed in the container by means of screw caps 36 with an O-ring so that they may be easily inserted in the container 1.

Instead of ampules we may use syringes with thin needles sealed with a glass tube which may be broken by the knives.

I claim:

1. Oceanographic water sampling means comprising, a container, cable means connected to the container to locate the container at a predetermined location in an ocean,
    cover means closably mounted on the container,
    means connected to close the cover means to trap a water sample, and
    means to add chemicals to the trapped water in the container at the same location where the sample is taken.

2. Apparatus as in claim 1, wherein the means to add chemicals comprises,
    means to mount ampules containing the chemicals in said container and means connected to break the ampules.

3. Apparatus as in claim 2, wherein the means to break the ampules includes a time delay device so that a first chemical may be added to the trapped water at a certain time, and the second chemical may be added to the trapped water after a predetermined time delay.

4. Apparatus as in claim 3, wherein the time delay device comprises a spring loaded piston.

5. Apparatus as in claim 2, wherein the cover means comprises a pair of covers.

6. Apparatus as in claim 2, wherein the means to break the ampules comprises a movable knife, and means to trigger movement of the knife.

* * * * *